US005580961A

United States Patent [19]
Saito et al.

[11] Patent Number: 5,580,961
[45] Date of Patent: *Dec. 3, 1996

[54] HETERODIMERIC T LYMPHOCYTE RECEPTOR SUBUNIT

[75] Inventors: Haruo Saito, Arlington; David M. Kranz, Somerville; Herman N. Eisen, Waban; Susumu Tonegawa, Chestnut Hill, all of Mass.

[73] Assignee: Massachusetts Institute of Technology, Cambridge, Mass.

[*] Notice: The term of this patent shall not extend beyond the expiration date of Pat. No. 4,874,845.

[21] Appl. No.: 210,326

[22] Filed: Mar. 18, 1994

Related U.S. Application Data

[62] Division of Ser. No. 742,539, Aug. 8, 1991, which is a continuation of Ser. No. 271,217, Nov. 14, 1988, abandoned, which is a division of Ser. No. 620,122, Jun. 13, 1984, Pat. No. 4,874,845.

[51] Int. Cl.$^6$ .......................... C07K 14/725; C07K 14/00
[52] U.S. Cl. .......................... 530/395; 530/386; 530/350; 530/324; 435/69.1
[58] Field of Search .................................. 530/386, 350, 530/324, 395; 435/69.1

[56] References Cited

PUBLICATIONS

Young et al. 1983. PNAS USA 80:1194–8.
Bigler et al. 1983. J. Exp. Med. 158:1000–5.
Itohara et al. 1989. PNAS USA 86:5094–8.
Galfre et al. 1981. Meth. Enzymol. 72:3–47.

*Primary Examiner*—Stephen G. Walsh
*Assistant Examiner*—Elizabeth C. Kemmerer
*Attorney, Agent, or Firm*—Arnall Golden & Gregory

[57] ABSTRACT

Disclosed is a heterodimeric T lymphocyte receptor subunit. The subunit consists of variable, joining, constant, transmembrane, and cytoplasmic regions.

The structure, amino acid, and nucleotide sequence of the lymphocyte receptor submit were determined using cDNA clones derived from a functional murine cytotoxic T lymphocyte clone. The genes corresponding to these cDNA are expressed and rearranged specifically in T cells and have significant sequence homologies to immunoglobulin V and C genes.

T cell receptor subunits may be produced from the cDNA clones. The protein molecules may be further used for the production of T-cell clone specific antibodies.

3 Claims, 8 Drawing Sheets

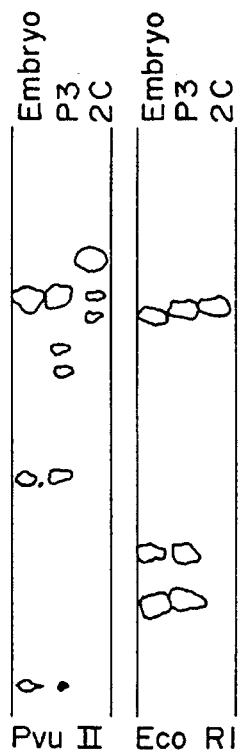
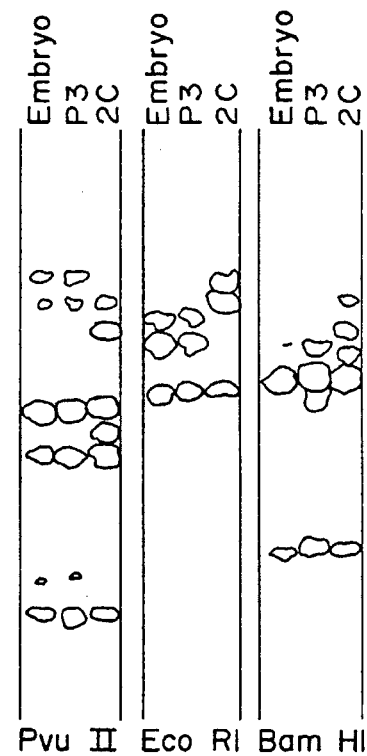
FIGURE 1a
FIGURE 1b
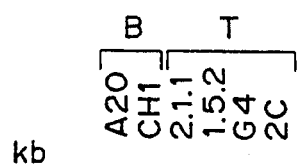
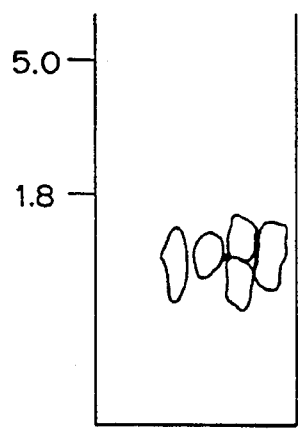
FIGURE 2a
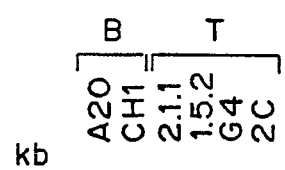
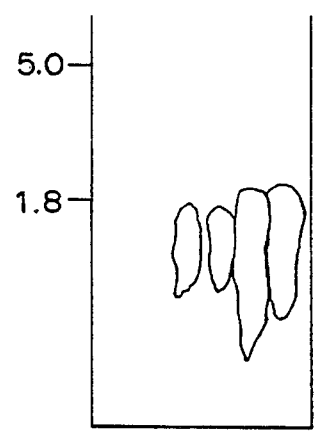
FIGURE 2b

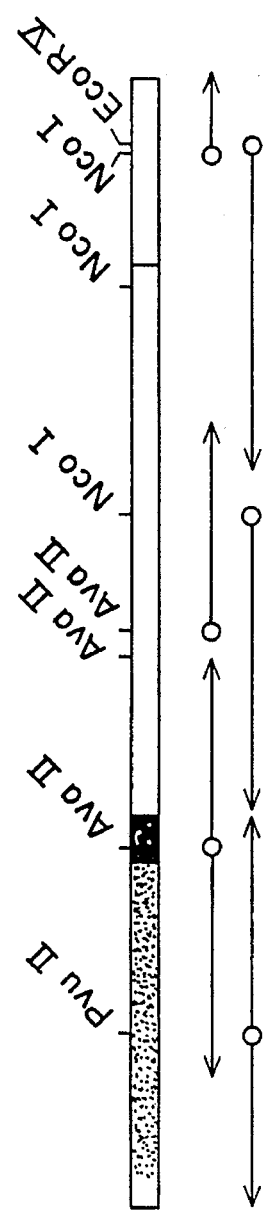
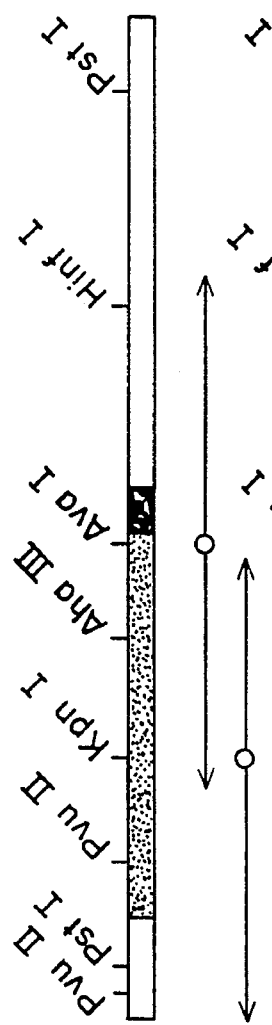
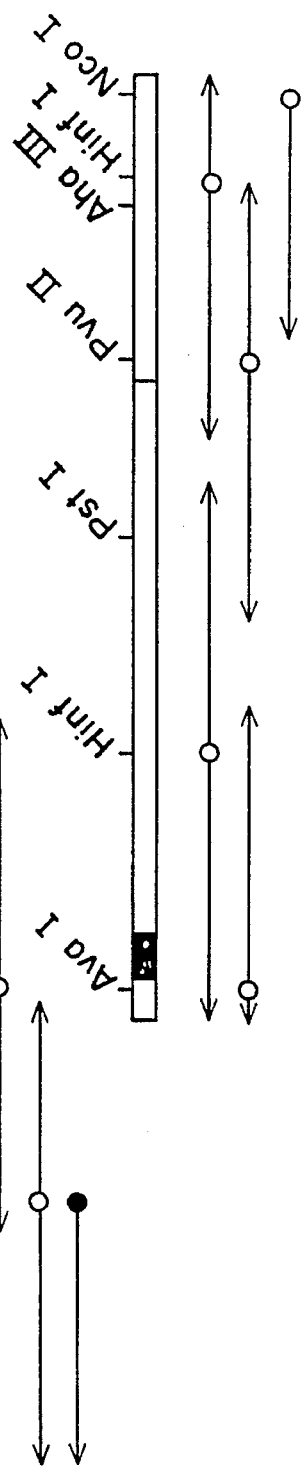
FIGURE 3A
FIGURE 3B

FIGURE 4A

```
      -11    V  V  L  C  F  L  G  T  G  L  V  D  M  K  V  T  Q  M  S  R  M  G  E  N  V  L  E  ©
             CT GTG GTC CTG TGT TTC CTA GGA ACA GGC CTT GTG GAC ATG AAA GTA ACC CAG ATG TCA AGA ATG GGA GAG AAT GTT TTG GAA TGT     104
                                                                    30           E                    50    Y                      90  F    A  Q
      G  Q  Q  D  H  M  S  H  T  M  Y  R  Q  D  P  G  L  G  L  L  I  Y  I  S  Y  T  N  Q  S  A  K  T  N  Q  S  V  Y  F  ©  A  Q
      GGA CAG CAG GAC CAT ATG AGC CAT ACA ATG TAC CGA CAA GAC CCT GGT CTG GGG CTA CAG CTG ATT TAT ATC TCA TAC ACA AAC CAG TCT GCT AAA ACA AAC CAG TCT GTG TAC TTC TGT GCG CAG    209
                                                         70                                80         S                              120 V                              160 E     H  S
      D  I  P  K  K  G  Y  Y  R  V  S  R  K  K  R  E  H  F  S  L  I  L  D  S  A  K  T  N  Q  T  S  L  F  E  P  S  K  A
      GAC ATC CCT AAA AAA GGA TAC TAC AGG GTC TCA CGG AAG AAG CGG GAG CAT TTC TCC CTG ATT CTG GAT TCT GCT AAA ACA AAC CAG ACA TCT GTG TAC TTC TGT GCG CAG
                    100                                           110                                                     150 V                              160 E  V  H  S
      G  A  P  E  Q  Y  F  G  Q  Y  F  P  G  T  R  L  T  V  L  E  D  L  R  N  V  T  P  P  K  V  S  L  F  E  P  S  K  A
      GGG GCG CCT GAA CAG TAC TTC GGT CAA TAC TTC CCC GGC ACT AGG CTC ACG GTT TTA GAG GAT CTG AGA AAT GTG ACT CCA CCC AAG GTC TCC TTG TTT GAG CCA TCA AAA GCA     419
                 130                                    140                                                     180                              190
      E  I  A  N  K  Q  K  A  T  L  V  ©  L  A  R  G  F  F  P  D  H  V  E  L  S  W  W  V  N  G  R  E  V  H  S
      GAG ATT GCA AAC AAA CAA AAG GCT ACC CTC GTG TGC TTG GCC AGG GGC TTC TTC CCT GAC CAC GTG GAG CTG AGC TGG TGG GTG AAT GGC AGG GAG GTC CAC AGT     524
                           170                                                     180                                        190
      G  V  S  T  D  P  Q  A  Y  K  E  S  N  Y  S  Y  C  L  S  S  R  L  R  V  S  A  T  F  W  H  N  P  R  N  H
      GGG GTC AGC ACG GAC CCT CAG GCC TAC AAG GAG AGC AAT TAT AGC TAC TGC CTG AGC AGC CGC CTG AGG GTC TCT GCT ACC TTC TGG CAC AAT CCT CGA AAC CAC     629
                 200                                    210                                                     220                              230
      F  R  ©  Q  V  Q  F  H  G  L  S  E  E  D  K  W  P  E  G  S  P  K  P  V  T  Q  N  I  S  A  E  A  W  G  R
      TTC CGC TGC CAA GTG CAG TTC CAT GGG CTT TCA GAG GAG GAC AAG TGG CCA GAG GGC TCA CCC AAA CCT GTC ACA CAG AAC ATC AGT GCA GAG GCC TGG GGC CGA     734
                                    240                                                250                                                                 ——TM——
      A  D  ©  G  I  T  S  A  S  Y  H  Q  G  V  L  S  A  T  I  L  Y  E  I  L  L  G  K  A  T  L  Y  A  V  L  V
      GCA GAC TGT GGA ATC ACT TCA GCA TCC TAT CAT CAG GGG GTT CTG TCT GCA ACC ATC CTC TAT GAG ATC CTA CTG GGG AAG GCC ACC CTA TAT GCT GTG CTG GTC     839
      ——270——                                                        ——→282
            S  G  L  V  L  M  A  M  V  K  K  K  N  S
      AGT GGC CTA GTG CTA ATG GCC ATG GTC AAG AAA AAA AAT TCC    TGAGACAAAC TTTTATGCAT CCTGAGCCCT TCTTCACCCT GCCATAGATT TTCCTGCACC TTCTCTAATT     951

CCTGTTCCTA AGAACTTGTC TCTTCTTCCT CCATGGATAT CCATCCTTCC TCGTTGACAC CTTGACTCTG AAACAGACTA AATCAATAAA AACATGGAGT TAA    1054
```

```
              1                   20                    40                    60                    80
2Cβ           DMKVTQMSRYLIKRMGENVLLECGQDMSHETMYWYRQDPG-LGLQLIYISYDVDSNSEGDIPKGYRVSRKKREHFSLILDSAKTNQTS-VYFCAQGAP---
2B4#71        NSKMIQTPRYLVKGQGQKAKMRCIPEKGHPVVFWYQQNKNNEFKFLINFQNQEVLQQIDMTEKRFSAECPSNSPCSLEIQS-SEAGDSALYLCASSLCS-Y
86T1          NTKITQSPRYLILGRANK-SLECEQHLGHNAMYWYKQSAEKPPE-LMFLYNLKQLIRNETVPSRFIPECPDSSKLLLHI-SAVDPEDSAVYFCASSHGQGY
```

HETERODIMERIC T LYMPHOCYTE RECEPTOR SUBUNIT

This is a divisional of U.S. Ser. No. 07/742,539, filed on Aug. 8, 1991, by Haruo Saito, David M. Kranz, Herman N. Eisen, and Susumu Tonegawa for "Heterodimeric T Lymphocyte Receptor Subunit," which is a continuation of U.S. Ser. No. 07/271,217, filed on Nov. 14, 1988, by Haruo Saito, David M. Kranz, Herman N. Eisen, and Susumu Tonegawa for "Heterodimeric T Lymphocyte Receptor Subunit" (now abandoned), which is a divisional of U.S. Ser. No. 06/620,122, filed on Jun. 13, 1984 by Haruo Saito, David M. Kranz, Herman N. Eisen, and Susumu Tonegawa for "Heterodimeric T Lymphocyte Receptor Subunit" (now U.S. Pat. No. 4,874,845)

BACKGROUND OF THE INVENTION

The U.S. government has rights in this invention by virtue of Grant No. NIH-5-PO1-CA28900-04, NIH-5-P30-CA14051-13 and the Arthritis Foundation.

The vertebrate immune system is characterized by its ability to respond to an enormously diverse set of antigenic determinants. This capability is due to the synthesis by the body of a set of glycoproteins whose specificity for a single antigen is determined by a variable sequence of amino acids which binds to the antigen. The glycoproteins, which recognize and bind free antigens, are produced by B cells and are called immunoglobulins (Ig).

Each B cell, or bone marrow-derived lymphocyte, produces antibody specific for only one antigen. It has been theorized that the type of immunoglobulin which is produced by the B cell is generated by a series of gene rearrangements and RNA splicing events that result in polypeptide chains consisting of variable and constant regions. These regions can be subdivided into domains held together by interchain and intrachain disulfide bridges situated at the same relative positions. The characteristic primary and secondary structure it made up of heavy and light chains which begin with a leader peptide of 17–29 residues, followed by a variable (V) region of 94–97 residues, then a joining region of 13–17 residues (J), then a constant region (C). The domains of the constant regions of the immunoglobulins are encoded by separate exons from those for the variable region and do not appear to rearrange during development.

T cells or Thymus derived lymphocytes, like B cells, are capable of recognizing a wide range of different antigens. The ability to recognize a given antigen is also fixed in any particular clonal line of T cell. T cells, however, recognize only antigens located on the surfaces of cells in the specific molecular context of self major histocompatability complex (MHC) gene products, not freely circulating antigens. Two types of T cell receptors have been proposed: those which recognize foreign antigens (such as vital antigens) in the molecular context of the T cell host's self-MHC gene products and those which recognize foreign MHC gene products. Cell surface antigens include tumor cell and viral antigens. The ability to recognize cell-bound antigens is acquired when the T cells differentiate in the host thymus.

Effective antisera and monoclonal antibodies have now been developed which recognize and precipitate clone-specific proteins on the surface of functional T cell clones, hybridomas or T cell tumors. Studies using these antibodies have suggested that the specificity—determining portion of a T cell receptor is a heterodimeric glycoprotein of about 90,000 daltons and consisting of a 40–45,000 dalton alpha subunit and a 42–44,000 dalton beta subunit. Peptide fingerprint analysis suggested that both subunits were composed of variable and constant regions.

Two groups of workers have since succeeded in isolating T cell-specific cDNA (complementary DNA) clones of mouse or human origin which are homologous to immunoglobulin genes. S. M. Hedrick, E. A. Nielsen, J. Kevaler, D. I. Cohen, and M. M. Davis, as reported in Nature, 308:153–158 (1984), have shown that the cDNA encodes a protein composed of an amino terminal variable an a carboxy-terminal constant region. They also showed that the corresponding genomic DNA sequences had undergone clone-specific somatic rearrangements in various T cell lines.

Y. Yanagi, Y. Yoshikai, K. Leggett, S. P. Clark, I. Aleksander, and T. W. Mak, in Nature, 308:145–149 (1984) reported the nucleotide sequence of a cDNA clone derived from the human leukaemic T cell line, MOLT-3. The predicted amino acid sequence encoded by the human cDNA clone of Yanagi et al. is highly homologous in the constant region to the cDNA clone isolated by Hedrick et al. from an antigen specific, MHC-restricted T helper cell hybridoma. Due to the substantial homology between the sequences of Hedrick et al and Yanagi et al it is likely that they represent one subunit of the T cell receptor.

It is therefore an object of the present invention to provide a T cell receptor gene or nucleotide sequence which code for subunits of the T cell receptor.

It is a further object of the present invention to provide murine cDNA clones which code for a subunit of the T cell receptor.

It is a still further object of the present invention to provide hybridization probes for identifying and isolating the T cell receptor genes and subunits of the T cell receptor genes of other, non-mouse species, including the human specie.

Another object of the present invention is to provide the protein or amino acid sequence of a murine alloreactive cytotoxic T lymptocyte receptor.

It is yet another object of the present invention to provide specific antibodies to the T cell receptor and subunits of the T cell receptor which are useful for identification, isolation, and in other methods for which antibodies are useful such as in delivering antibody bound drugs to a specific cell.

SUMMARY OF THE INVENTION

Complete nucleotide and amino acid sequences for T cell receptor subunits derived from the alloreactive cytotoxic T lymphocyte (CTL) clone 2C, of BALB.B origin and specific for the D end of the BALB/c H-2 complex (d haplotype) are disclosed. Two related but distinct cDNA clones corresponding to the gamma and beta subunits of T cell receptors were cloned and sequenced. The genes corresponding to these cDNA are expressed and rearranged specifically in T cells and have sequence hemologies to immunoglobulin variable and constant region genes. The constant region sequence of the beta subunit is compared to the constant region sequence of the beta subunit of a T helper cell and found to correspond. It is therefore concluded that the disclosed T cell specific cDNA sequences for the constant region of at least the beta subunit and probably the gamma subunit may be used to produce protein, and antibody to that protein, which are useful in isolation, identification, and other methods for both cytotoxic T lymphocytes and T helper cells. Expected species to species homology among mammalian organisms, including man, further extends possible applications of the present invention.

BRIEF DESCRIPTION OF THE DRAWINGS

FIG. 1 is a Southern blot analysis of DNA from BALB/c embryos, myeloma P3 (BALB/c derived), and CTL 2C (BALB.B). DNA was digested with the indicated restriction enzymes, electrophoresed through 0.8% agarose, blotted onto nitrocellulose, and hybridized with $^{32}$p-labelled, nick-translated inserts from clone pHDS11 (a) or clone pHDS4 (b). Separate experiments showed that BALB/c and BALB.B embryo patterns are indistinguishable.

FIG. 2 is a RNA blot analysis of poly A$^+$ RNA from various B and T cell lines. RNA was extracted from B cell lymphoma, A20-2J and CH1 and alloreactive (H-2$^b$ anti H-2$^d$), cytotoxic T lymphocyte clones 2.1.1, 1.5.2, G4, and 2C. Approximately 1.5 micrograms of poly A$^+$ RNA were denatured with glyoxal and electrophoresed through 1% agarose in 10 mM sodium phosphate buffer, pH 6.5. RNA was transfered to nitrocellulose and hybridized to $^{32}$P-labelled, nick translated inserts from clone pHDS11 (a) or clone pHDS4 (b). Positions of rRNA markers (5.0 and 1.8 kilobase) are as indicated.

FIG. 3a and 3b illustrates restriction maps of the inserts of (FIG. 3b) cDNA clones isolated from CTL 2C, clone pHDS11 (FIG. 3a) and clones pHDS203 and pHDS4. The maps were constructed by the standard single, double, or triple digestions of the plasmid DNA. The V, J, C, and 5' or 3' untranslated regions are designated by , , , and , respectively. Also shown is the sequencing strategy employed to produce the nucleotide sequences shown in FIG. 4. The 5'- and 3'-end labellings are indicated by ○ and ●, respectively.

FIG. 4 lists the determined nucleotide and predicted amino acid sequences of cDNA clones pHDS11 (a) and pHDS4/pHDS203 (b). The numbers given above the amino acid sequences designate the residue positions. The numbers at the right end of the Figure are for nucleotide positions. The negative numbers are for predicted signal peptides. The V, J, C, TM (transmembrane) and CY (cytoplasmic) regions are indicated although the exact boundaries are somewhat ambiguous. The cysteins thought to be involved in intradomain or interchain disulfide linkages are indicated. The two nucleotides that are different in the C or 3'-untranslated regions of pHDS11 and 2B4#71 are indicated by *. The oligonucleotide thought to be a signal for the poly A attachment site is underlined in (b).

FIG. 5(a) is a comparisons of the predicted amino acid sequences of three $V_{beta}$ regions, $2C_{beta}$ (pHSD11), 2B4#71, and 86T1. Those residues common between $2C_{beta}$ and 2B4#71, or 2B4#71 and 86T1 are indicated by vertical lines.

DETAILED DESCRIPTION OF THE PREFERRED EMBODIMENT

Figure 5B:
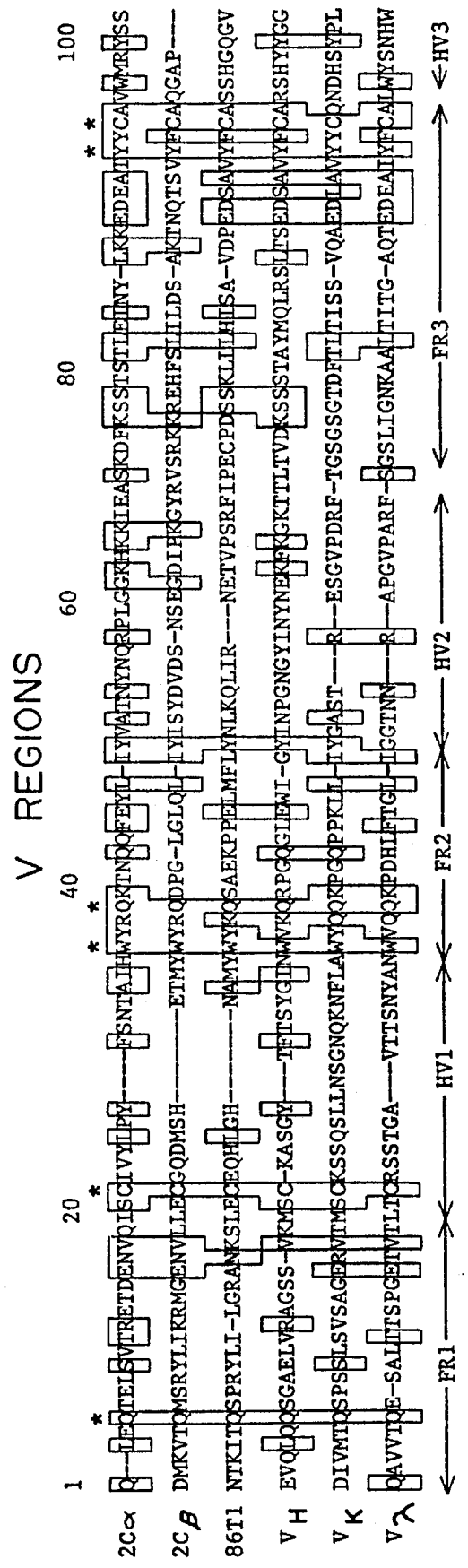
FIG. 5(b) is a comparison of the predicted amino acid sequence of pHDS4/203 and predicted or determined amino acid sequences of five other proteins, the beta chain encoded by pHDS11, the beta chain encoded by cDNA clone, 86T1, the V regions of 93G7$_{lambda\,1}$ heavy chain, CH1 region of μ heavy chain, the V and C regions of MOPC603 kappa chain, and MOPC104E$_{lambda\,1}$ chain. Those residues common between the pHDA4/203 polypeptide chain and any of the other five chains are shaded. The residues common among all six chains are indicated by *. Approximate boundaries of framework and hypervariable regions as they appear in Ig V regions are indicated by arrows.
Figure 5B:
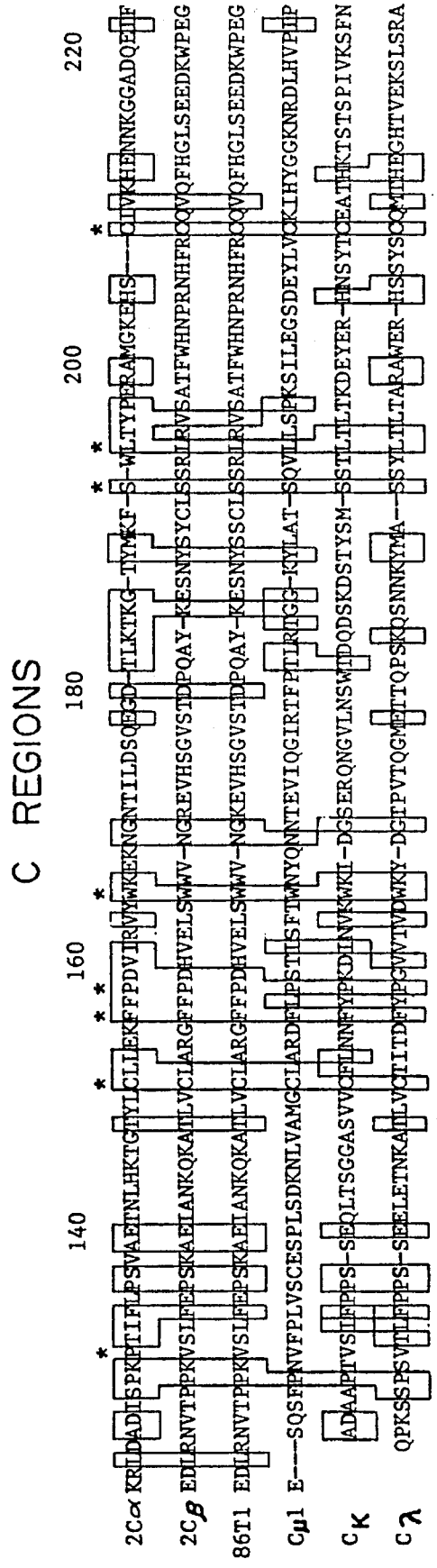

The preferred embodiment of the present invention is the structure and possible amino acid and nucleotide sequences of subunits of a heterodimeric glycoprotein which functions as a receptor on the surface of a T lymphocyte. The invention also includes cDNA hybridization probes and antibodies for the identification and isolation of T cell receptors from other species as well as from cytotoxic and helper T cells. The T cell receptor and the nucleotide and amino acid sequences required to produce the protein or its components are defined by their substantial identity to the proposed tertiary structure and nucleotide and amino acid sequences of the receptor of a murine alloreactive cytotoxic T lymphocyte.

T cell receptors are made up of two chains, each with two extracellular Ig-like domains, an amino-terminal variable domain, and a carboxy-terminal constant domain. Each of these domains is stabilized by a disulfide bond between cysteine residues. The gamma chain, consisting of 286 amino acid residues, has cysteine residues at amino acid residues 21, 94 (variable region), 151,207 (constant region), 234 (adjacent transmembrane region), and 280 (cytoplasmic region). The beta chain, consisting of 282 amino acid residues, has cysteine residues at amino acid residues 23, 91 (variable region), 140, 201 (constant region) and 236 (adjacent transmembrane region). The variable region of the gamma subunit, consisting of codons 1–102, is joined to the constant region by codons 103–117. The variable region of the beta subunit, consisting of codons 1–96, is joined to the constant region by 97–109. Beyond the constant domain, each subunit has at its carboxyl-end a hydrophobic stretch of 21–22 amino acids followed by a short stretch of 5 (beta subunit) or 12 (gamma subunit) amino acid residues in which cationic residues abound. These segments correspond respectively, to the transmembrane and cytoplasmic domains characteristically found in transmembrane proteins.

The variable and constant regions are coded for by distinct gene segments. The same gene appears to code for at least the beta chain constant region of cytotoxic T-lymphocytes and the beta chain constant region of helper T cells. The variable regions of cytotoxic T-lymphocytes (CTL) and helper T cells are probably coded for by non-overlapping gene segments. The apparent homology between the amino acid sequences of constant regions of both helper T cells and CTL enables one to use hybridization probes and antibodies directed against the constant region of the beta chain of the T receptor of either cell type to identify and isolate the T receptor of the other cell type.

The invention will be further understood from the following non-limiting example wherein the amino acid and nucleotide sequences and hybridization probes for an alloreactive CTL clone are provided. All of the starting materials for this procedure are readily available to those skilled in the art from commercial or other sources.

Isolation of T cell-specific cDNA clones

T cell-specific cDNA clones were isolated from the alloreactive CTL clone 2C, of BALB.B (mouse) origin and specific for the D end of the BALB/c H-2 complex (d haplotype). This clone was described by D. M. Kranz, D. H. Sherman, M. V. Sitkovsky, M. S. Pasternack, and H. N. Eisen in *Proc. Natl. Acad Sci USA*, 81:573–577 (1984).

The cDNA (complementary DNA) synthesized on the poly $A^+$ RNA from 2C was subtracted twice with poly $A^+$RNA from a mouse B cell lymphoma, A20-2J, according to the method of Hedrick et al. in *Nature* 308:149–153 (1984). The B cell lymphoma, described by D. J. McKean, A. J. Infante, A. Nilson, M. Kimoto, C. G. Fathman E. Walker and N. Warner, *J. Exp. Med.*, 154:1419–1431 (1981) was used to remove cDNA that cross reacted with B lymphocytes rather than being specific for T lymphocytes. The method of Hedrick et al. is as follows:

(1) $^{32}$p-labelled cDNA is synthesized from cytoplasmic poly $(A)^+$ RNA of a T cell using oligo (dT) and reverse transcriptase;

(2) the RNA template is depleted by base hydrolysis;

(3) the cDNA is hybridized with B-cell mRNA such as B-cell lymphoma line poly $(A)^+$ RNA from Bal 12 or $MBT_H{}^{-B}$; and (4) unbound cDNA is removed by hydroxyapatite chromatography as T-cell specific cDNA.

A library of cDNA from the CTL clone 2C was constructed from the subtracted cDNA using the vector pBR 322 and a standard $^{dC\cdot}$dG tailing method, such as the one described by T. Maniatis, E. F. Fritsch, J. Sambrook in *Molecular Cloning, A Laboratory Manual*, p. 218, 269–307 (Cold Spring Harbor Laboratory, 1982). The library was screened using two hybridization probes. The first was the 2C cDNA prepared from the poly $A^+$ RNA of membrane-bound polysomes followed by subtraction with poly $A^+$ RNA from a second B cell lymphoma, CH1, described by M. A. Lynes, L. L. Lanier, G. F. Babcock, P. J. Wettstein, and G. Haughton in *J. Immunol.*, 121:2352–2357 (1978). The second was the cDNA prepared from the total poly $A^+$ RNA from the B cell lymphoma A20-2J.

The 2C-specific cDNA clones were identified and their plasmid DNA used as hybridization probes in a series of RNA blotting experiments in order to confirm the T cell-specific expression of the corresponding genes. The T cell-specific cDNA were grouped into sets according to the sizes of the corresponding mRNA present in 2C. One probe was found to be for the T cell specific cell surface marker Thy-1 on the basis of its hybridization to a previously identified Thy-1 cDNA clone provided by Mark Davis.

Identification of two distinct classes of T cell-specific cDNA clones whose genes are rearranged in CTL's.

Representative cDNA clones of each set of T cell-specific cDNA grouped according to its size were used as ,. hybridization probes. Comparison of this cDNA with EcoRI-digested genomic DNA from 2C and BALB.B embryos by the Southern gel blotting method led to identification of two distinct classes of cDNA, one represented by clone pHDS11 and the other by clones pHDS4 and pHDS203.

FIGS. 1a and 1b show the results of Southern gel blotting analysis using clone pHDS11(a) and pHDS4(b) as hybridization probes. The hybridization patterns obtained by the two probes following digestion with PvuII, EcoRI, and Bam HI restriction enzymes are clearly distinct, confirming that the two classes of cDNA clones represent two different sets of genes that do not cross hybridize to a detectable level under the conditions used. The patterns obtained with 2C DNA are different from the patterns obtained with BALB embryo DNA. The myeloma P3 DNA patterns are the same as the embryo DNA patterns.

DNA from five additional CTL clones were analyzed in the same fashion and also gave patterns different from those of embryo DNA with at least one enzyme. These results strongly suggest that genes corresponding to both cDNAs have undergone gross sequence rearrangement in 2C.

The T cell-specific expression of the genes corresponding to these DNA clones was confirmed by analyzing poly $A^+$ RNA from 2C and three other independently derived alloreactive CTL and B lymphomas, A20-2J and CH1. As shown in FIGS. 2a and 2b, each of the two cDNA probes detected RNA of distinct sizes in all four CTL but not in either of the B lymphomas, although the relative content, and in some cases the size, of the RNA was somewhat variable from one CTL to another. When analyzed with the clone pHDS11 probe CTL 2C, 1.5.2 and 2.1.1 all gave a major RNA component of about 1,300 bases while CTL G4 contained two major components of 1,400 and 1,200 bases. All four CTL gave a 1,500 base RNA component with the clone pHDS4 probe.

Nucleotide Sequence Analyses

As shown in FIG. 3a and b restriction maps of the three cDNA clones, pHDS11, pHDS4, and pHDS203, were constructed using standard procedures such as the ones described by T. Maniatis, E. F. Fritsch, J. Sambrook in *Molecular Cloning, A Laboratory Manual*, p. 3–54, 374–401 (Cold Spring Harbor Laboratory 1982) and the DNA sequences determined using the method of A. M. Maxam and W. Gilbert in *Methods in Enzymology*, L. Grossman and V. Moldave, Editors, 65:499–560 (Academic Press, N.Y. 1980).

pHDS11

Figure 4B:
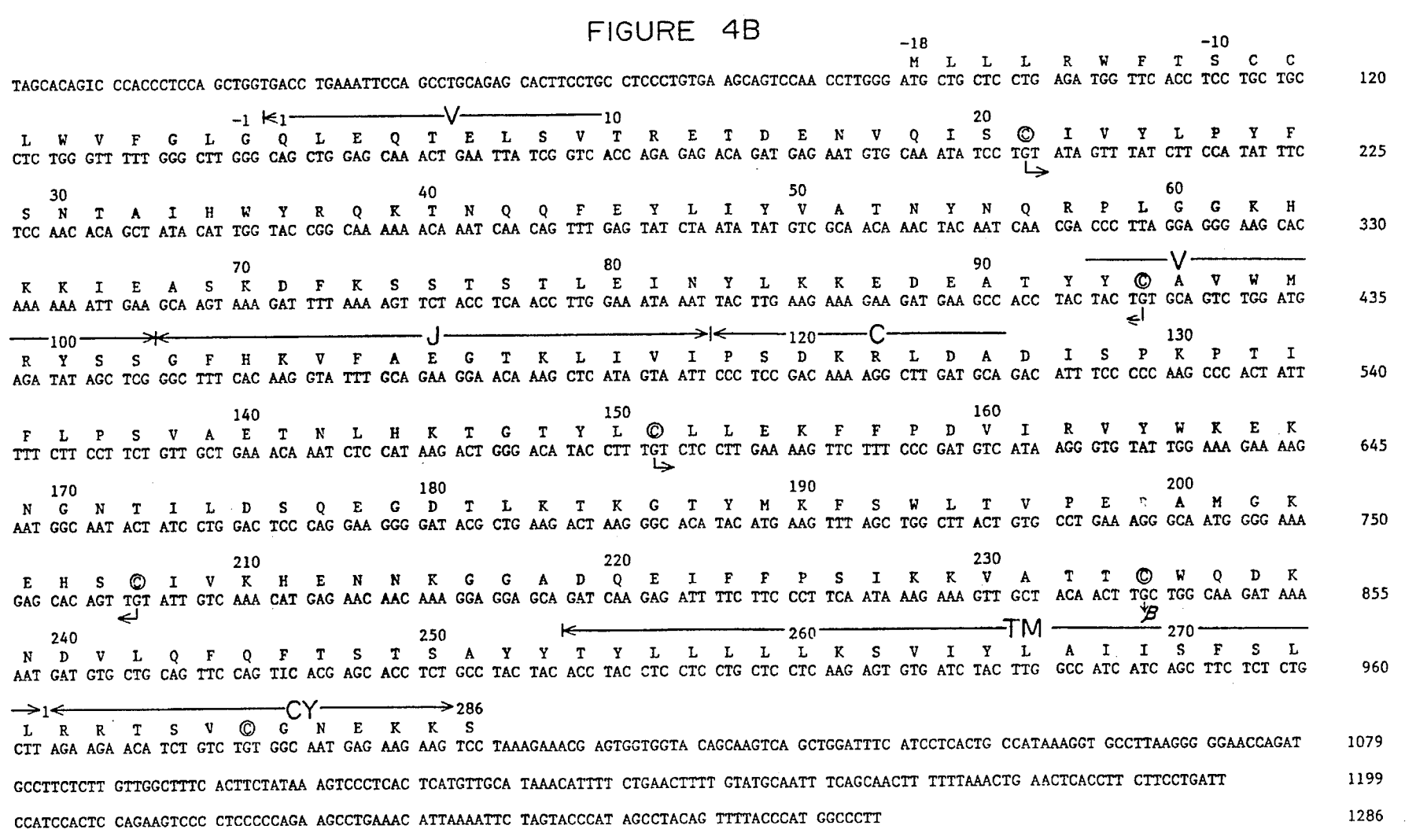

The entire nucleotide sequence of the 1,054 base pair insert of clone pHDS11 is shown in FIG. 4(a). The longest open reading frame is composed of an 879 nucleotide stretch whose corresponding amino acid sequence of 293 residues is also shown in FIG. 4(a). The codons are numbered starting with the triplet GAC at nucleotide position 36–38. There is a stretch of about dozen highly hydrophobic residues at the 5' end of the open reading frame that probably comprise part of a signal peptide. Homology between the pHDS11 protein and immunoglobulin variable regions (V), particularly $V_k$ regions, suggests that Asp at position 1 is the N-terminal residue. The variable region is between codons 1 and 96 and the joining region from codons 97 to 109.

The major body of the constant region is defined by codons 110 (Glu) and 236 (Cys). Codon 236 (Cys) is prior to the N-terminus of the transmembrane segment (TM) which extends from codon 256 to 277. The constant region pHDS11 sequence is identical to the sequence of the corresponding region of the thymocyte cDNA clone, 86T1, described by Hedrick et al. except for one base pair in codon 159.

The sequence identity of the constant region between pHDS11 and 2B4#71 from a cDNA clone isolated from a T helper cell (T$_H$) hybridoma specific for anti pigeon cytochrome C is also striking. The T$_H$ cDNA clone is described by Yih Chien, N. R. J. Gascoigne, J. Kevaler, N. E. Lee, and M. M. Davis in *Nature* (in press).

The two sequences are identical throughout the constant regions and the entire 3' untranslated region except for two base pair differences at codon 159 and at nucleotide positions 992.

Figure 6:
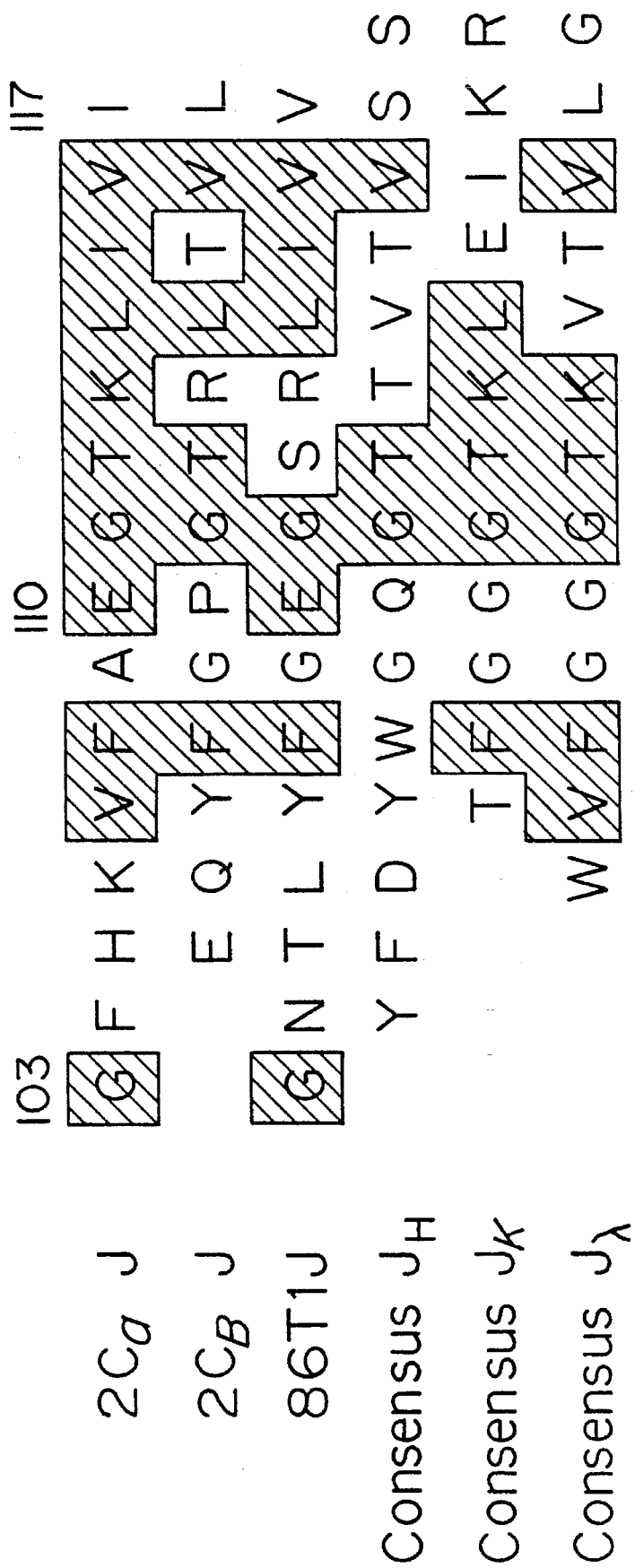
FIG. 6 shows comparisons of the J region sequence of 2Cgamma (predicted from pHDS4/203) and those of $2C_{beta}$ (predicted from pHDS11), 86T1, and Ig $J_H$, $J_{kappa}$ and $J_{lambda}$ consensus sequences. Those residues common between 2Cgamma J and any one of the other 5J's are boxed in and shaded.

The joining region from codons 97 to 109 in the pHDS11 sequence is distinct from 8671 and 2B4#71, but homologous to the joining segments of Ig genes. As shown in FIG. 6, the pHDS11 joining sequence corresponds exactly to the sequence of the $^J$T$^7$ genomic segment recently identified and characterized by Chien et al.

As shown in FIG. 5(a), the pHDS11 sequence between codons 1 and 96 is quite different from the corresponding region of either 86T1 or 2B4#71. There are areas of conserved residues between the three sequences, however, and between these sequences and the immunoglobulin variable regions of both heavy and light chains, in particular, the two cysteine residues involved in intradomain disulfide linkages and the Trp residue at residue 34.

Another stretch of a highly conserved hydrophobic region of about 22 residues, immediately between the C-terminal five hydrophilic residues constitutes a transmembrane (TM) peptide. The five hydrophilic residues are thought to extend into the cytoplasm.

Overall, the gene defined by pHDS11 can encode a process protein of 282 residues with a molecular weight of 33,000 daltons. There are four potential sites for N-glycosylation.

pHDS4 and pHDS203

The composite nucleotide sequence of 1286 base pairs defined by the two overlapping clones pHDS4 and pHDS203 is shown in FIG. 4(b). The encoded amino acid sequence is also shown.

The longest open reading frame begins with the Met codon at nucleotide positions 88–90, extends over a stretch of 912 base pairs and ends at nucleotide position 999. As shown in FIGS. 5(b) and 6, this sequence is significantly homologous to those of pHDS11, 86T1, 93 G7 Ig heavy chain, MOPC/603 Ig k light chain and MOPC/104E Ig$_{lambda1}$ light chain. The homology in the variable region is between 18 and 23%, the homology in the joining region is between 21 and 50%, and the homology in the constant region is between 16 and 22%. The homology occurs in patches which tend to correspond to the framework regions (FR) of the variable regions of immunoglobulins. Residues shared by the five non pHDS4/203 and pHDS4/203 include the cysteine residues involved in intradomain disulfide linkages as well as the Trp residue which is universally present at the boundary of the firs hypervariable (HV-I) and FR-2 segments of all immunoglobulin variable regions studied to date.

The peptide at the amino terminal end of the, pHDS4/203 protein is highly hydrophobic and is probably a signal peptide. Since this prevents unambiguous determination of the N-terminal amino acid of the processed protein, the N-terminal residue, Gln at position 1, is implied from the fact that N-terminal residue of the alpha subunit of the T cell receptor is blocked, probably by a pyrollidone carboxylic acid residue, and that this places the first conserved cysteine residue at position 21 which corresponds to the cysteine residue at position 22 or 23 in the corresponding immunoglobulin variable regions.

The pHDS4/203 protein contains a second hydrophobic peptide of about 20 residues near its carboxy terminus which is probably a transmembrane peptide. This region is followed by a hydrophilic C-terminal segment of 12 residues which most likely comprises an intracytoplasmic peptide. The processed protein is 286 residues long and the calculated molecular weight is 33,000 daltons.

SUMMARY

On the basis of T cell-specific expression, T cell-specific rearrangement, and sequence homology to immunoglobulin chains and to the beta chain purified by Reinherz et al. (personal communication) from a T cell tumor REX, the cDNA clones reported by Hedrick et al., Yanagi et al., and Chien et al., have been shown to code for the beta subunit of the mouse and human T cell receptor. Since the pHDS11 gene is expressed and rearranged in CTL but not in B lymphoma cells and the.. C-terminal half of the protein encoded by this gene is highly homologous or identical to the corresponding regions of the proteins encoded by the clones reported by Yanagi et al., Hedric et al., and Chien et al., it can be concluded that clone pHDS11 encodes for the beta subunit of CTL2C.

The gene defined by cDNA clones pHDS4 and pHDS203 is also expressed and rearranged specifically in T cells. It is clearly distinct from and does not crosshybridize with under standard conditions the beta chain gene. The pHDS4/203 sequence is 16–23% related to the beta chain, the same as to immunoglobulin light and heavy chains. There is striking organizational similarity between the two proteins: each has two immunoglobulin-like domains, a transmembrane peptide, and a cytoplasmic peptide of similar size. The pHDS4/203 protein is very similar in size (32,000 daltons) to the size of the beta chain encoded by pHDS11. Both sequences contain one cysteine in corresponding positions, 234 and 236 respectively, that lie outside of the Ig-like domains.

Figure 7:
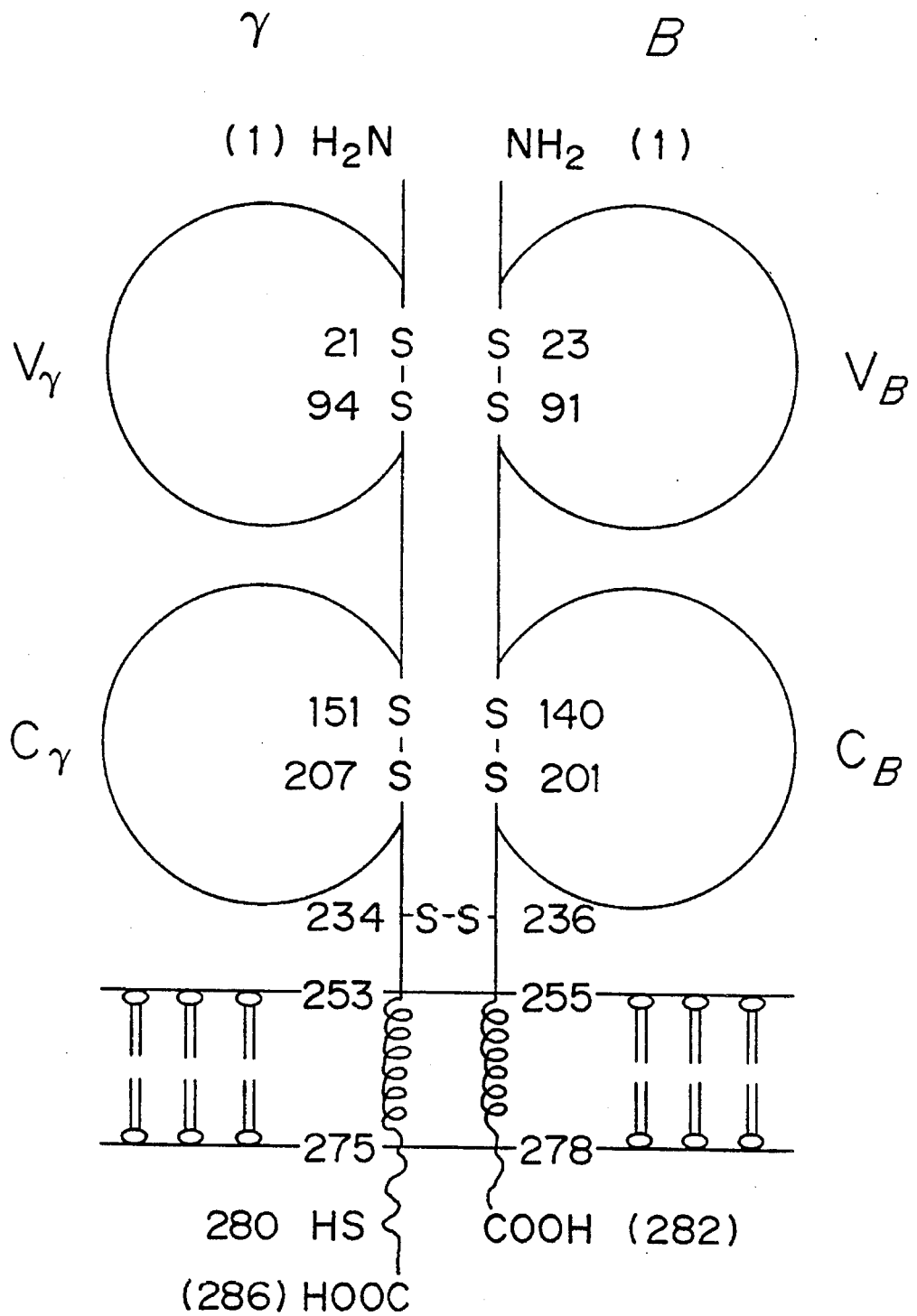
FIG. 7 shows the proposed overall structure of a receptor. Each receptor molecule is made up of two chains, each with two extracellular Ig-like domains, an amino-terminal variable and a carboxy-terminal constant domain. Each of these domains is stabilized by an S—S bond between cysteine residues. Two chains are held by a single interchain S—S bond located close to the cell's outer membrane. The protein is anchored on the membrane by two (one for each chain) hydrophobic transmembrane peptides. A short carboxy-terminal peptide rich in cationic residues extends into the cytoplasm in each chain. The SH group of the cystein residue present in the cytoplasmic peptide of the alpha subunit may interact dynamically with a membrane or cytoplasmic protein and thereby may be important for the cell's effector function. Both chains are glycosylated, although the exact site(s) and extent of glycosylation have not yet been determined.

A proposed structure for the T cell receptor is shown in FIG. 7. The receptor molecule is made up of two chains, each with extracellular immunoglobulin-like domains, an amino-terminal variable and a carboxy-terminal constant domain. Each domain is stabilized by a disulfide bond between cysteine residues.

The molecular weights of the gamma and beta subunits are each less by about 10,000 daltons than the apparent molecular weight observed in SDS-polyacrylamide gel electrophoresis. It is possible this difference is due to N-glycosylation of the beta subunit and O-glycosylation on serine and threonine residues of the gamma subunit.

A stable association between two subunits may be required to form an effective binding region, as is characteristic of immunoglobulins. The obligate participation of two different subunits in the formation of a single combining site means that combinational variability is likely to contribute to structural and functional diversity of these receptors.

The presence of 21–22 hydrophobic amino acids followed by a stretch of amino acid residues in which there are many cationic residues at the carboxyl-end of the constant domain corresponds to the transmembrane and cytoplasmic domains that are characteristically found in transmembrane proteins.

The presence of a cysteine residue in the cytoplasmic domain of the gamma subunit might provide an SH group for dynamic interactions with other molecules of the cell membrane, such as T3 in human CTL, or perhaps the cytoskeleton. The need for a functional association with such accessory structures is suggested by the resemblance of the proposed T cell receptor model to the Fab fragments of immunoglobulin molecules.

Considering the high sequence homology observed between two corresponding genes belonging to two mammalian species (for example, mouse Ig $C_k$ and human Ig $C_k$ are 60% homologous, mouse Ig $C_{lambda}$ and human Ig $C_{lambda}$ are 65% homologous, rabbit $C_{H2}$ and human $C_{H2}$ are 63% homologous, and rabbit $C_{H3}$ and human $C_{H3}$ are 66% homologous (Davis et al, *Microbiology*, 2nd Ed., p. 441 (Harper & Row Publishers, 1973) and compare homology between the gene sequence of Hedrick et al and Yanagi et al for the beta subunit of the T cell receptor), it is highly probable that the gamma and beta genes of different mammalian species, including human, can be cloned from the T cell cDNA libraries of these species using the disclosed mouse gamma and beta cDNA as hybridization probes.

The cDNA may be used in various systems known to those skilled in the art to make large quantities T cell receptor protein. This is of tremendous use since a major limitation on previous work was the small amount of T cell receptor available for study. Both procaryotic and eucaryotic systems are useful for production of T cell receptor protein or the alpha or beta subunits of the receptor.

An example of a method of producing protein from the cDNA is taught by copending application U.S. Ser. No. 592,231, to Gillies et al., entitled "Enhanced Production of Proteinaceous Materials in Eucaryotic Cells" and filed Mar. 22, 1984, now U.S. Pat. No. 4,663,281.

Another method is taught by Gray and Goeddel, entitled "Cloning and Expression of Murine Immune Interferon cDNA" *Proc Natl. Acad. Sci. USA.*, 80:5842–5846 (1983).

The eucaryotic system has the advantage over the procaryotic system that the expressed molecule is glycosylated.

The T cell receptor protein or polypeptide sequences may be used for further studies, in systems for the detection of anti-T cell antibodies, and in other procedures known to those skilled in the art. They may also be used for the production of specific T cell receptor antibodies which are directed against the gamma or beta subunit, or specific regions within the subunits, such as the constant region. The antibodies directed against the constant region of the cytotoxic T lymphocyte should be equally effective against the constant region of T helper cells.

Antibodies may be produced from the protein or its subunits using conventional techniques known to those skilled in the art. Nucleotide sequences may also be utilized to produce short peptides or oligonucleotides which are then bound to a carrier protein such as bovine serum albumin (BSA) for injection into an animal for the production of antibodies. For example, an animal may be immunized against the protein or peptide or oligonucleotide bound protein and immunoglobulin isolated from the serum. The B cells from the immunized animal with the desired specificity may also be fused with a cell line which is maintained in cell culture, such as myelomas or other tumor cell lines, to form hybridomas for the continuous production of antibody.

Antibodies are useful in isolation procedures such as by affinity chromatography wherein antibody is bound to a solid matrix and by precipitation of soluble antibodies in solution. Antibodies are useful in analysis and identification using any of a number of well known techniques. A recently developed use of antibodies involves binding an agent, such as a drug, to the antibody, then injecting the bound antibody into a patient so that the drug is delivered only to the desired site. In the present invention, an example of such a use would be delivery of a chemotherapeutic compound to malignant T cells in a patient with a T cell lymphoma.

The invention may be embodied in other specific forms without departing from the spirit and scope thereof. These and other modifications of the invention will occur to those skilled in the art. Such other embodiments and modifications are intended to fall within the scope of the appended claims.

What is claimed is:

1. A glycoprotein functioning as a gamma subunit in a naturally occurring T cell receptor for antigens and MHC gens products when located on the surface of a T lymphocyte, comprising a variable region specific for at least one MHC gene product;

a constant region of a gamma subunit of a naturally occurring T cell receptor comprising an amino acid sequence having substantial identity to a corresponding amino acid sequence in a T lyphocyte from another source;

a joining region of a gamma subunits of a naturally occurring T cell receptor comprising an amino acid sequence connecting said variable and said constant region;

a transmembrane region of a gamma subunit of a naturally occurring T cell receptor comprising a sequence of predominantly hydrophobic amino acids; and a cytoplasmic region of a gamma subunit of a naturally occurring T cell receptor comprising a sequence of predominantly cationic amino acids; wherein the glycoprotein is not present on a T-cell.

2. A glycoprotein comprising:

a gamma subunit of a naturally occurring T cell receptor comprising a sequence of 286 amino acid residues wherein said sequence for the gamma subunit consists of a variable region of 102 amino acid residues, a joining region of 15 amino acid residues between said variable region and a constant region of 135 amino acid residues, a transmembrane region of 21 amino acid residues, and a cytoplasmic region of 12 amino acids; wherein the glycoprotein is not present on a T-cell.

3. The constant region of the gamma subunit of a naturally occurring T lymphocyte receptor; wherein the constant region is not present on a T-cell.

* * * * *